(12) United States Patent
Wu et al.

(10) Patent No.: US 11,497,587 B2
(45) Date of Patent: Nov. 15, 2022

(54) ORAL SCANNER

(71) Applicant: Qisda Corporation, Taoyuan (TW)

(72) Inventors: Tsung-Hsun Wu, Taoyuan (TW);
Yung-Tsun Hsieh, Taipei (TW);
Hao-Chieh Li, Taipei (TW)

(73) Assignee: Qisda Corporation, Taoyuan (TW)

( * ) Notice: Subject to any disclaimer, the term of this patent is extended or adjusted under 35 U.S.C. 154(b) by 960 days.

(21) Appl. No.: 16/263,002

(22) Filed: Jan. 31, 2019

(65) Prior Publication Data

US 2019/0247163 A1 Aug. 15, 2019

(30) Foreign Application Priority Data

Feb. 13, 2018 (CN) .......................... 201810149991.8

(51) Int. Cl.
| | |
|---|---|
| *A61C 9/00* | (2006.01) |
| *A61B 5/00* | (2006.01) |
| *A61C 13/15* | (2006.01) |
| *F28D 21/00* | (2006.01) |
| *A61B 1/253* | (2006.01) |

(52) U.S. Cl.
CPC ............ *A61C 9/0053* (2013.01); *A61B 1/253* (2013.01); *A61B 5/0084* (2013.01); *A61C 19/004* (2013.01); *F28D 2021/0029* (2013.01)

(58) Field of Classification Search
None
See application file for complete search history.

(56) References Cited

U.S. PATENT DOCUMENTS

2002/0182563 A1* 12/2002 Boutoussov ............ F21V 29/74
433/29
2013/0141558 A1* 6/2013 Jeon ...................... G01J 1/0233
250/353

FOREIGN PATENT DOCUMENTS

| CN | 104200758 A | | 12/2014 | |
|---|---|---|---|---|
| CN | 104378537 A | * | 2/2015 | |
| CN | 105796046 A | * | 7/2016 | |
| CN | 105796046 A | | 7/2016 | |
| GB | 2256938 A | | 12/1992 | |
| WO | WO-9731293 A1 | * | 8/1997 | ............ A61B 1/253 |

OTHER PUBLICATIONS

Wikipedia, "6061 aluminum alloy", posted on Dec. 19, 2017 (Year: 2017).*
Office action of counterpart application by State Intellectual Property Office of the People's Republic of China dated Sep. 30, 2019.

* cited by examiner

*Primary Examiner* — Yingchun He

(57) ABSTRACT

The present invention discloses an oral scanner, including an outer casing, a reflector, a heat source, an optical module and a forced convection element. The outer casing has a cavity. The reflector is located at the front end of the cavity. The heat source is located in the outer casing. The optical module is located in the casing. A heat channel is formed between the optical module and the outer casing. The forced convection element is disposed in the heat channel and configured to forcedly dissipate the waste heat of the heat source to the cavity to heat the reflector. Thus, the temperature of the heat source can be reduced, and vapor will not be generated on the reflector heated by the waste heat.

20 Claims, 3 Drawing Sheets

ORAL SCANNER

This application claims the benefit of People's Republic of China application Serial No. 201810149991.8, filed on Feb. 13, 2018, the subject matter of which is incorporated herein by reference.

BACKGROUND OF THE INVENTION

Field of the Invention

The invention relates in general to an oral scanner, and more particularly to an oral scanner with forced convection element.

Description of the Related Art

When the oral scanner is operated inside the oral cavity, vapor, which negatively affects the image capture quality of the oral scanner, will be generated on the optical lens of the oral scanner if the temperature inside the oral cavity is different from the temperature inside the oral scanner. Therefore, it has become a prominent task for the industries to avoid vapor being generated on the optical lens of the oral scanner.

SUMMARY OF THE INVENTION

The invention is directed to an oral scanner whose forced convection element dissipates the waste heat of the heat source to the cavity of the outer casing to heat the reflector.

According to one embodiment of the present invention, an oral scanner, including an outer casing, a reflector, a heat source, an optical module and a forced convection element, is provided. The outer casing has a cavity. The reflector is located at the front end of the cavity. The heat source is located in the outer casing. The optical module is located in the casing. A heat channel is formed between the optical module and the outer casing. The forced convection element is disposed in the heat channel and configured to forcedly dissipate the waste heat of the heat source to the cavity to heat the reflector.

As an optional technical solution, the outer casing includes a front section having a cavity and a through hole interconnected with the cavity. The oral scanner further includes a lens disposed in the through hole. The front section has a heat transfer coefficient between 0.3 cal/cm·s·° C. and 0.4 cal/cm·s·° C.

As an optional technical solution, the outer casing includes a front section having a cavity. The front section is a metal piece, which conducts the waste heat to the reflector to heat the reflector directly.

As an optional technical solution, the outer casing includes a front section having a cavity and a through hole interconnected with the cavity. The cavity becomes an open space through the through hole. The front section is a plastic piece.

As an optional technical solution, the oral scanner further includes a first divider located between the reflector and the optical module. The optical path of the optical module passes through the first divider. The first divider has a third opening interconnecting the cavity and the heat channel.

As an optional technical solution, the forced convection element has a fluid entrance and a fluid exit; and the oral scanner further includes a second divider and a carrier. The second divider is configured to connect the outer casing and isolate the fluid entrance from the fluid exit. The carrier is configured to carry the forced convection assembly. The carrier and the second divider are integrally formed in one piece.

As an optional technical solution, the heat source is a circuit board.

As an optional technical solution, the oral scanner further includes a temperature sensor and a controller. The temperature sensor is located in the cavity to detect the temperature inside the cavity. The controller is configured to turn off the operation of the optical module when the temperature inside the cavity is higher than the pre-set temperature value, the operation of the heat source and the operation of the forced convection element, or turn off the operation of the optical module and the operation of the heat source but maintain the operation of the forced convection assembly.

As an optional technical solution, the oral scanner further includes a temperature sensor and a controller. The temperature sensor is located in the cavity to detect the temperature inside the cavity. The controller is configured to increase the rotation speed of the forced convection element when the temperature inside the cavity is higher than the pre-set temperature value.

As an optional technical solution, the controller is further configured to turn off the operation of the optical module and the operation of the heat source if the temperature inside the cavity is still higher than the pre-set temperature value after the rotation speed of the forced convection element has been increased over a period of time.

In comparison to the current technology, the oral scanner disclosed in the present invention includes an outer casing, a reflector, a heat source, an optical module and a forced convection element. The outer casing has a cavity. The reflector is located at the front end of the cavity. The heat source is located in the outer casing. The optical module is located in the casing. A heat channel is formed between the optical module and the outer casing. The forced convection element is disposed in the heat channel and configured to forcedly dissipate the waste heat of the heat source to the cavity to heat the reflector. Thus, the temperature of the heat source can be reduced, and vapor will not be generated on the reflector heated by the waste heat.

The above and other aspects of the invention will become better understood with regard to the following detailed description of the preferred but non-limiting embodiment(s). The following description is made with reference to the accompanying drawings.

DETAILED DESCRIPTION OF THE INVENTION

Figure 1:
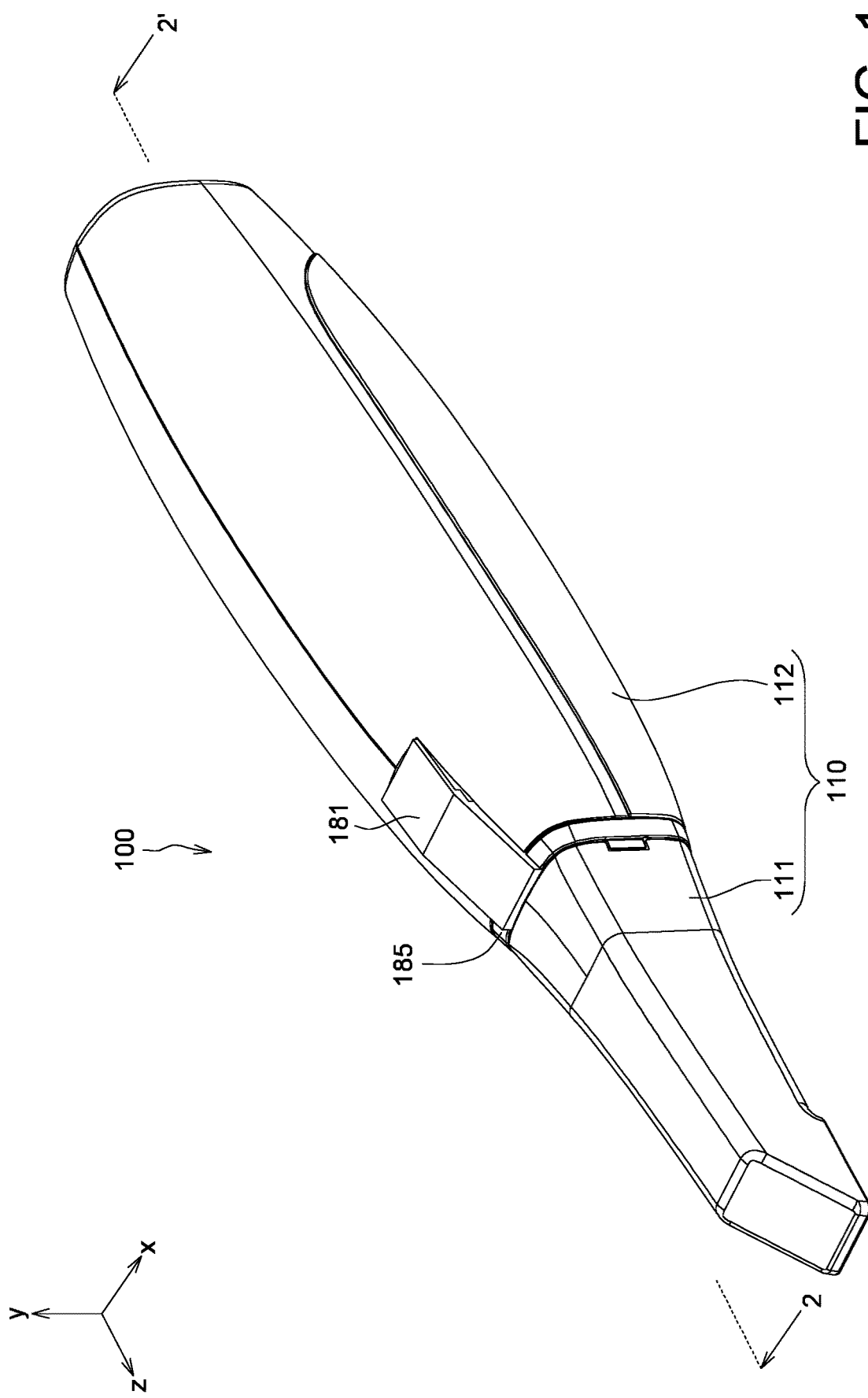
FIG. 1 is a schematic diagram of an oral scanner according to an embodiment of the present invention.
Figure 2:
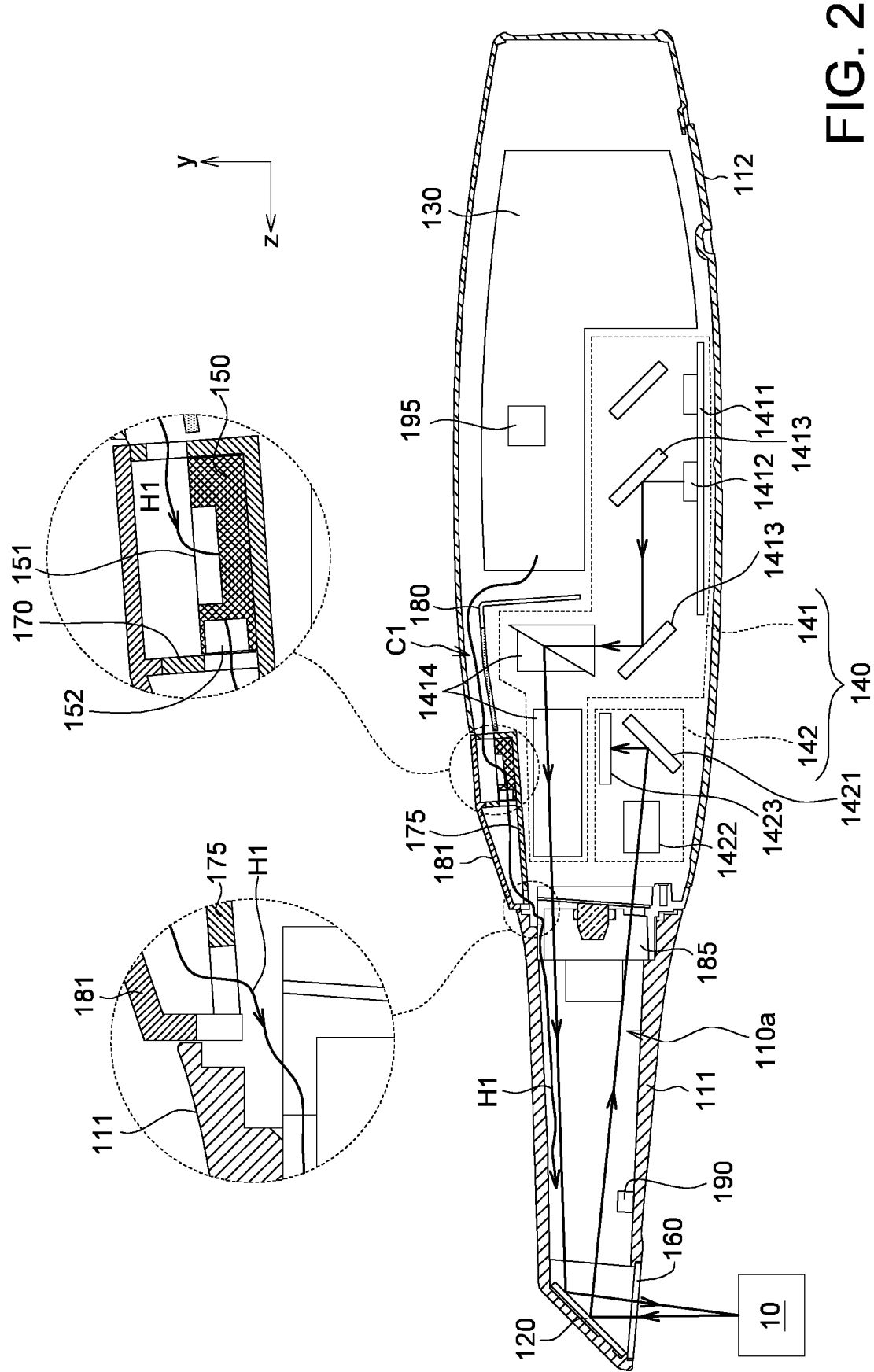
FIG. 2 is a cross-sectional view of the oral scanner of FIG. 1 along a direction 2-2'.

Refer to FIG. 1 and FIG. 2. FIG. 1 is a schematic diagram of an oral scanner 100 according to an embodiment of the present invention. FIG. 2 is a cross-sectional view of the oral scanner 100 of FIG. 1 along a direction 2-2'.

The oral scanner 100 includes an outer casing 110, a reflector 120, a heat source 130, an optical module 140, a forced convection element 150, a lens 160, a second divider 170, a carrier 175, a thermal guide 180, a first divider 185, a temperature sensor 190 and a controller 195.

The outer casing 110 has a cavity 110a. The reflector 120 is located at the front end of the cavity 110a. The heat source 130 is located in the outer casing 110. The optical module 140 is located in the outer casing 110. A heat channel C1 is formed between the optical module 140 and the outer casing 110. The forced convection element 150 is disposed in the heat channel C1 and configured to forcedly dissipate the waste heat H1 of the heat source 130 to the cavity 110a to heat the reflector 120 and avoid vapor being generated on the reflector 120 and affecting the image capture quality. To summarize, according to the embodiment of the present invention, without using any additional heater, the reflector 120 can be heated by the waste heat generated by existing element of the oral scanner 100 to avoid vapor being generated on the reflector 120. In addition, the design of guiding the waste heat H1 generated by the heat source 130 to the cavity 110a can reduce the temperature of the heat source 130 and avoid the heat source 130 getting too hot and becoming damaged.

In the present embodiment, the heat source 130 can be a circuit board. However, the source of the waste heat H1 is not limited to the heat source 130. Any elements of the oral scanner 100 that generate heat, such as any elements of the optical module 140, can be a source of the waste heat H1.

As indicated in FIG. 2, the optical module 140 includes a projection module 141 and an image capture module 142. The projection module 141 includes a circuit board 1411, at least one light emitting element 1412, at least one first reflector 1413 and a first lens assembly 1414. The light emitting element 1412 is disposed on the circuit board 1411 and electrically connected thereto. The light emitting element 1412 can emit a detection light L1 to the unit under test 10 along a first optical path to scan the profile of a unit under test 10. The first optical path sequentially passes through the at least one first reflector 1413, the first lens assembly 1414 and the reflector 120. The unit under test 10 can be any tissue, such as a tooth, inside the oral cavity. The image capture module 142 includes at least one second reflector 1421, a second lens assembly 1422 and an image sensing element 1423. The image capture light L2 is reflected to the image sensing element 1423 from the unit under test 10 along a second optical path. The image sensing element 1423 can sense a profile image of the unit under test 10. The second optical path sequentially passes through the second lens assembly 1422 and at least one second reflector 1421.

Moreover, the forced convection element 150 can be realized by a fan, such as an axial fan or a centrifugal fan. As indicated in FIG. 2, the carrier 175 carries the forced convection assembly 150. The forced convection element 150 has a fluid entrance 151 and a fluid exit 152. The waste heat H1 is absorbed to the forced convection element 150 via the fluid entrance 151, and is then dissipated via the fluid exit 152. The second divider 170 is connected to the outer casing 110 and isolate the fluid entrance 151 from the fluid exit 152. Thus, the waste heat H1 dissipated from the fluid exit 152 will not be refluxed to the fluid entrance 151 and the heat channel C1.

As indicated in FIG. 2, the thermal guide 180 is disposed at the upper stream of the forced convection element 150, such that the heat channel C1 between the thermal guide 180 and the outer casing 110 is closer to the heat source 130 for guiding more or most of the waste heat H1 of the heat source 130 to the forced convection assembly 150. Thus, the temperature of the heat source 130 can be effectively reduced and/or the utilization rate of the waste heat H1 can be increased.

As indicated in FIG. 1 and FIG. 2, the outer casing 110 includes a front section 111 and a rear section 112. When operating the oral scanner 100, the operator can grab the rear section 112 and extend the front section 111 to the inside of the oral cavity.

As indicated in FIG. 1 and FIG. 2, the front section 111 has a cavity 110a and a through hole 111a interconnected with the cavity 110a. The lens 160 is disposed in the through hole 111a. The front section 111 has a heat transfer coefficient between 0.3 cal/cm·s·° C. and 0.4 cal/cm·s·° C. The heat transfer coefficient can also be smaller than 0.3 cal/cm·s·° C. or larger than 0.4 cal/cm·s·° C. Since the heat transfer coefficient of the front section 111 is high, even when the through hole 111a is sealed by the lens 160 (the cavity 110a becomes a closed space or a near closed space), the waste heat H1 still can be conducted to the outer surface of the front section 111 due to the high thermal conductivity of the front section 111, and is further convected to the outside of the oral scanner 100 to avoid the front section 111 getting too hot and damaging the oral cavity. Furthermore, the front section 111 with high heat transfer coefficient can directly conduct the waste heat H1 to the reflector 120 to heat the reflector 120 directly. In an embodiment, the front section 111 is a metal piece formed of a metal such as copper, aluminum or an alloy thereof. In an exemplary embodiment, the front section 111 can be formed of AL 6061 whose heat transfer coefficient is about 0.37 cal/cm·s·° C. In the embodiment of the present invention, the material of the front section 111 is not specified.

In another embodiment, the oral scanner 100 can omit the lens 160. That is, the through hole 111a does not have any physical elements disposed therein, such that the cavity 110a becomes an open space through the through hole 111a. Under such design, the heat transfer coefficient of the front section 111 can be smaller than the heat transfer coefficient of the front section (such as a metal piece). For example, the heat transfer coefficient of the front section 111 is smaller than 0.3 cal/cm·s·° C. or smaller than 0.4 cal/cm·s·° C. Since the cavity 110a is an open space, even when the heat transfer coefficient of the front section 111 is low, the waste heat H1 still can be convected to the outside of the oral scanner 100 through the opening 111a to avoid the front section 111 getting too hot and scalding the oral cavity. In the present embodiment, the front section 111 can be a plastic piece or can be formed of other material such as engineering plastics whose heat transfer coefficient is low or is not too high.

As indicated in FIG. 2, the rear section 112 is connected to the front section 111. The heat source 130, the optical module 140, the forced convection element 150, the second divider 170, the carrier 175, the thermal guide 180, the first divider 185 and the controller 195 can be disposed in the rear section 112. The rear section 112 can be formed of a material with low heat transfer coefficient (such as plastics) to avoid the operator's hand being scalded. However, in the embodiment of the present invention, since the waste heat H1 still can be guided to the cavity 110a of the front section 111, even when the rear section 112 is formed of a material whose heat transfer coefficient is not low (such as metal), the operator's hand is unlikely to be scalded.

In addition, the temperature sensor 190 is located in the cavity 110a to detect the temperature inside the cavity 110a. Preferably but not necessarily, the temperature sensor 190 is disposed close to the lens 160 or the reflector 120. The controller 195 is disposed on the circuit board (such as the heat source 130) and electrically connected to at least one electronic element of the heat source 130, the optical module 140, the forced convection element 150 and the temperature sensor 190. The controller 195 is configured to, when the temperature inside the cavity 110a is higher than the pre-set temperature value, turn off the operation of the optical module 140, the operation of the heat source 130 and the operation of the forced convection assembly 150 to reduce the waste heat H1 and avoid the oral scanner 100 getting too hot and scalding the oral cavity or the operator's hand. In the present specification, the pre-set temperature value is between Celsius 40° to Celsius 60°. The pre-set temperature value can also be smaller than Celsius 40° or larger than Celsius 60°.

In another embodiment, the controller 195 is configured to, when the temperature inside the cavity 110a is higher than the pre-set temperature value, increase the rotation speed of the forced convection element 150 to enhance the convection of the waste heat H1 to reduce the temperature of the oral scanner 100 and avoid the oral scanner 100 getting too hot and scalding the oral cavity or the operator's hand.

In other embodiments, the controller 195 is configured to turn off the operation of the optical module 140 and the operation of the heat source 130 to reduce the generation of the waste heat H1 and avoid the oral scanner 100 getting too hot and scalding the oral cavity or the operator's hand if the temperature inside the cavity 110a is still higher than the pre-set temperature value after the rotation speed of the forced convection assembly 150 has been increased over a period of time.

In other embodiments, the controller 195 is configured to, when the temperature inside the cavity 110a is higher than the pre-set temperature value, turn off the operation of the optical module 140 and the operation of the heat source 130 but maintain the operation of the forced convection assembly 150 to more quickly reduce the temperature inside the cavity 110a and avoid the oral scanner 100 getting too hot and scalding the oral cavity or the operator's hand.

Figure 3A:
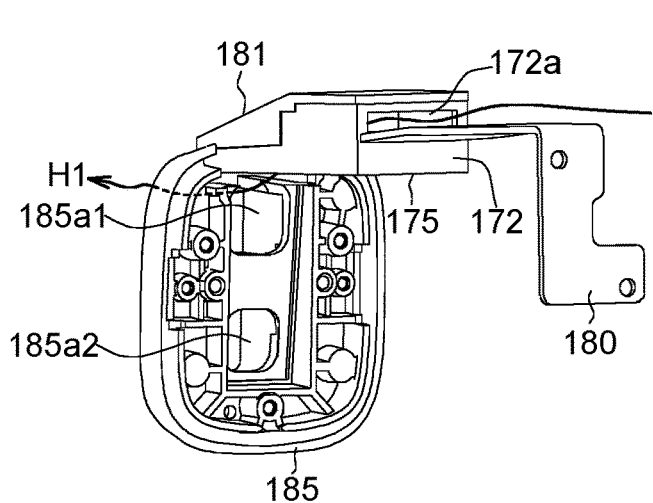
FIG. 3A and FIG. 3B are schematic diagrams of the carrier, the thermal guide and the cover of FIG. 2.
Figure 3B:
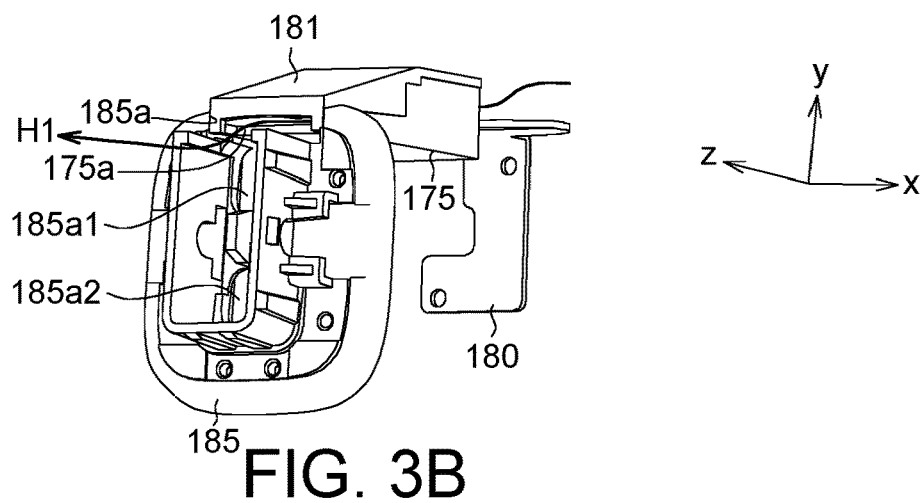
Figure 3C:
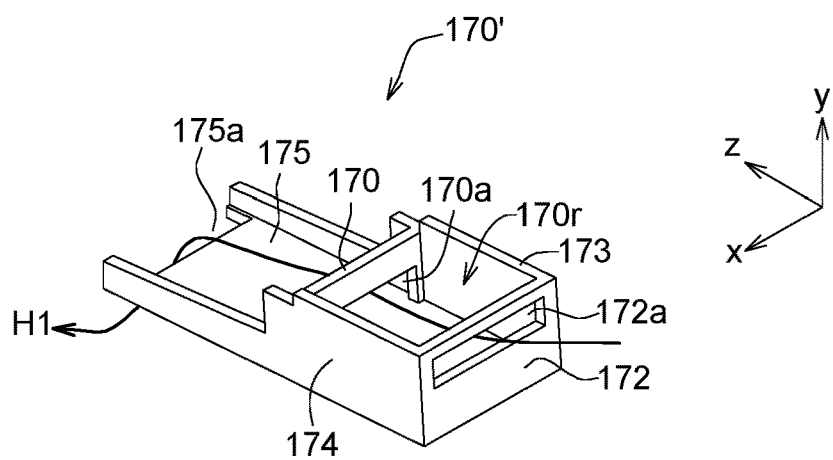
FIG. 3C is a schematic diagram of the second divider and the carrier of FIG. 3A.

Refer to FIGS. 3A to 3C. FIG. 3A and FIG. 3B are schematic diagrams of the carrier 175, the thermal guide 180, the first divider 185 and the cover 181 of FIG. 2. FIG. 3C is a schematic diagram of the second divider 170 and the carrier 175 of FIG. 3A.

As indicated in FIG. 3C, the second divider 170 and the carrier 175 of the present embodiment are integrally formed in one piece. For example, the second divider 170 and the carrier 175 form a carrier box 170', wherein the carrier 175 can be the bottom plate of the carrier box 170', the second divider 170 can be the first side plate of the carrier box 170', and the bottom plate and the first side plate are interconnected with each other. The carrier box 170' further includes a second side plate 172, a third side plate 173 and a fourth side plate 174, all are connected to the carrier 175. The second side plate 172 and the second divider 170 are disposed oppositely, and the third side plate 173 and the fourth side plate 174 are disposed oppositely to form an accommodation portion 170r. The forced convection assembly 150 (not illustrated) can be disposed in the accommodation portion 170r.

As indicated in FIG. 3A to FIG. 3C, the second side plate 172 has an entrance 172a. The second divider 170 has a first opening 170a. The waste heat H1 enters the accommodation portion 170r via the entrance 172a. Then, the waste heat H1, after passing through the forced convection assembly 150 (not illustrated), is dissipated via the first opening 170a. The carrier 175 has a second opening 175a. After the waste heat H1 dissipated from the first opening 170a passes through the second opening 175a, the waste heat H1 is dissipated to the cavity 110a. As indicated in FIG. 3C, the third side plate 173 and the fourth side plate 174 do not have any openings, hence reducing the leakage of the waste heat H1 and increasing the utilization rate of the high waste heat H1. Also, the carrier box 170' can be formed of a material with low heat transfer coefficient (such as plastics), which avoids the waste heat H1 being dissipated off the oral scanner 100 before entering the cavity 110a and therefore increases the utilization rate of the waste heat H1.

As indicated in FIG. 2, the first divider 185 is located between the reflector 120 and the optical module 140. The optical path of the optical module 140 passes through the first divider 185. As indicated in FIG. 3A and FIG. 3B, the first divider 185 has a first optical channel 185a1 and a second optical channel 185a2, respectively allowing a detection light L1 and an image capture light L2 emitted by the optical module 140 to pass through. The first divider 185 has a third opening 185a interconnected with the first optical channel 185a1. In another example, the division plate (not illustrated) of the first divider 185 isolates the third opening 185a from the first optical channel 185a1 and prevents the waste heat H1 passing through the third opening 185a from flowing to the first optical channel 185a1, and therefore reduces the negative influence caused to the light passing through the first optical channel 185a1 by the waste heat H1. As indicated in FIG. 2, the cover 181 and the carrier box 170' are connected to the third opening 185a. For example, the cover 181 and the carrier box 170' are engaged with the third opening 185a. The third opening 185a interconnects the cavity 110a and the second opening 175a, and is further interconnected with the heat channel C1 (illustrated in FIG. 2) through the second opening 175a, the first opening 170a and the entrance 172a. Thus, the waste heat H1 inside the heat channel C1 can sequentially pass through the entrance 172a, the first opening 170a, the second opening 175a and the third opening 185a to be dissipated to the cavity 110a.

As indicated in FIG. 3A and FIG. 3B, the cover 181 covers the carrier box 170', such that the leakage of the waste heat H1 inside the carrier box 170' can be reduced, and the utilization rate of the waste heat H1 can be increased. Moreover, the cover 181 can be formed of a material with low heat transfer coefficient (such as plastics), which avoids the waste heat H1 being dissipated off the oral scanner 100 before entering the cavity 110a and therefore increases the utilization rate of the waste heat H1.

To summarize, the oral scanner disclosed in the above embodiments of the present invention at least includes a forced convection assembly configured to forcedly dissipate the waste heat of the heat source to the cavity to heat the reflector. Thus, the temperature of the heat source can be reduced, and the reflector can be heated to avoid vapor being generated on the reflector. In an embodiment, the outer casing of the oral scanner can directly absorb the waste heat and then conduct the waste heat to the reflector to heat the reflector directly. Or, the waste heat inside the cavity can be convected to the reflector to heat the reflector. In an embodiment, the waste heat inside the oral scanner can be convected to the exterior due to the high thermal conductivity of the outer casing (such as metal) or through the through hole of the outer casing to avoid the oral scanner getting too hot and/or scalding the oral cavity. Or, the temperature sensor of the oral scanner can detect the internal temperature of the oral scanner. Based on the detected temperature, the controller can suitably adjust the rotation speed of the forced convection element and turn off the operation of the optical module, the operation of the heat source and/or the operation of the forced convection element to control the temperature of the oral scanner to avoid the oral scanner getting too hot and scalding the oral cavity and/or the operator's hand. Since the temperature of the oral scanner is not too high, the light will not be affected by the high temperature, and the image capture quality can therefore be maintained or even enhanced.

While the invention has been described by way of example and in terms of the preferred embodiment (s), it is to be understood that the invention is not limited thereto. On the contrary, it is intended to cover various modifications and similar arrangements and procedures, and the scope of the appended claims therefore should be accorded the broadest interpretation so as to encompass all such modifications and similar arrangements and procedures.

What is claimed is:

1. An oral scanner, comprises:
   an outer casing having a cavity;
   a reflector located at a front end of the cavity;
   a heat source located in the outer casing;
   an optical module located in the casing, wherein a heat channel is formed between the optical module and the outer casing; and
   a forced convection element disposed in the heat channel and configured to forcedly dissipate waste heat of the heat source to the cavity to heat the reflector;
   wherein the heat channel travels through the heat source, the forced convection element and the reflector in order.

2. The oral scanner according to claim 1, wherein the outer casing comprises a front section having a cavity and a through hole interconnected with the cavity, and the oral scanner further comprises:
   a lens disposed in the through hole;
   wherein, the front section has a heat transfer coefficient ranging between 0.3 cal/cm·s·° C. and 0.4 cal/cm·s·° C.

3. The oral scanner according to claim 1, wherein the outer casing comprises a front section having a cavity; the front section is a metal piece which conducts the waste heat to the reflector to directly heat the reflector.

4. The oral scanner according to claim 1, wherein the outer casing comprises a front section having a cavity and a through hole interconnected with the cavity, the cavity becomes an open space through the through hole, and the front section is a plastic piece.

5. The oral scanner according to claim 1, further comprises:
   a first divider located between the reflector and the optical module, wherein an optical path of the optical module passes through the first divider, and the first divider has a third opening interconnecting the cavity and the heat channel.

6. The oral scanner according to claim 1, wherein the forced convection element has a fluid entrance and a fluid exit; and the oral scanner further comprises:
   a second divider configured to connect the outer casing and isolate the fluid entrance from the fluid exit; and
   a carrier configured to carry a forced convection assembly;
   wherein the carrier and the second divider are integrally formed in one piece.

7. The oral scanner according to claim 1, further comprises:
   a carrier configured to carry a forced convection assembly;
   a first divider located between the reflector and the optical module; and
   a second divider configured to connect the outer casing and isolate a fluid entrance of the forced convection element from a fluid exit of the forced convection element;
   wherein the second divider, the carrier and the first divider have a first opening, a second opening and a third opening interconnecting the cavity and the heat channel; and
   wherein the waste heat inside the heat channel is allowed to sequentially pass through the first opening, the second opening and the third opening to be dissipated to the cavity.

8. The oral scanner according to claim 1, further comprises:
   a carrier configured to carry a forced convection assembly;
   a first divider located between the reflector and the optical module;
   a second divider configured to connect the outer casing and isolate a fluid entrance of the forced convection element from a fluid exit of the forced convection element; and
   a cover;
   wherein the second divider and the carrier form a carrier box, the cover covers the carrier box, and the cover and the carrier box are connected to the first divider.

9. The oral scanner according to claim 8, wherein the cover is formed of plastics.

10. The oral scanner according to claim 1, wherein the heat source is a circuit board.

11. The oral scanner according to claim 1, further comprises:
    a temperature sensor located in the cavity to detect temperature inside the cavity; and
    a controller configured to turn off an operation of the optical module, an operation of the heat source and an operation of the forced convection element when the temperature inside the cavity is higher than a pre-set temperature value.

12. The oral scanner according to claim 1, further comprises:
    a temperature sensor located in the cavity to detect temperature inside the cavity; and
    a controller configured to turn off an operation of the optical module and an operation of the heat source but maintain operation of a forced convection assembly when the temperature inside the cavity is higher than a pre-set temperature value.

13. The oral scanner according to claim 1, further comprises:
    a temperature sensor located in the cavity to detect temperature inside the cavity; and
    a controller configured to increase a rotation speed of the forced convection element when the temperature inside the cavity is higher than a pre-set temperature value.

14. The oral scanner according to claim 13, wherein the controller is further configured to:
    turn off an operation of the optical module and an operation of the heat source if the temperature inside the cavity is still higher than a pre-set temperature value after a rotation speed of the forced convection element has been increased over a period of time.

15. An oral scanner, comprises:
    an outer casing having a cavity;
    a reflector located at a front end of the cavity;

a heat source located in the outer casing;
an optical module located in the casing, wherein a heat channel is formed between the optical module and the outer casing; and
a forced convection element disposed in the heat channel and configured to forcedly dissipate waste heat of the heat source to the cavity to heat the reflector;
wherein the outer casing comprises a front section and a rear section connected with the front section, the heat source is disposed within the rear section, the reflector is disposed within the front section, and the heat channel travels to the reflector from the heat source.

16. The oral scanner according to claim 15, further comprises:
a first divider located between the reflector and the optical module, wherein an optical path of the optical module passes through the first divider, and the first divider has a third opening interconnecting the cavity and the heat channel.

17. The oral scanner according to claim 15, wherein the forced convection element has a fluid entrance and a fluid exit; and the oral scanner further comprises:
a second divider configured to connect the outer casing and isolate the fluid entrance from the fluid exit; and
a carrier configured to carry a forced convection assembly;
wherein the carrier and the second divider are integrally formed in one piece.

18. An oral scanner, comprises:
an outer casing having a cavity;
a reflector located at a front end of the cavity;
a heat source located in the outer casing;
an optical module located in the casing, wherein a heat channel is formed between the optical module and the outer casing; and
a forced convection element disposed in the heat channel and configured to forcedly dissipate waste heat of the heat source to the cavity to heat the reflector;
wherein the oral scanner further comprises:
a first divider located between the reflector and the optical module, wherein an optical path of the optical module passes through the first divider, and the first divider has a third opening interconnecting the cavity and the heat channel.

19. The oral scanner according to claim 18, wherein the forced convection element has a fluid entrance and a fluid exit; and the oral scanner further comprises:
a second divider configured to connect the outer casing and isolate the fluid entrance from the fluid exit; and
a carrier configured to carry a forced convection assembly;
wherein the carrier and the second divider are integrally formed in one piece.

20. The oral scanner according to claim 18, further comprises:
a temperature sensor located in the cavity to detect temperature inside the cavity; and
a controller configured to turn off an operation of the optical module, an operation of the heat source and an operation of the forced convection element when the temperature inside the cavity is higher than a pre-set temperature value.

* * * * *